US010457200B2

(12) United States Patent
Gage et al.

(10) Patent No.: US 10,457,200 B2
(45) Date of Patent: Oct. 29, 2019

(54) ABANDONED OCCUPANT DANGER ALERT SYSTEM

(71) Applicants: Michael T. Gage, Garland, TX (US); Robert H. Frantz, Oklahoma City, OK (US)

(72) Inventors: Michael T. Gage, Garland, TX (US); Robert H. Frantz, Oklahoma City, OK (US)

( * ) Notice: Subject to any disclaimer, the term of this patent is extended or adjusted under 35 U.S.C. 154(b) by 0 days.

(21) Appl. No.: 16/131,202

(22) Filed: Sep. 14, 2018

(65) Prior Publication Data

US 2019/0009715 A1  Jan. 10, 2019

Related U.S. Application Data

(63) Continuation-in-part of application No. 15/634,920, filed on Jun. 27, 2017, now Pat. No. 10,217,344.

(51) Int. Cl.
| | |
|---|---|
| *G08B 21/02* | (2006.01) |
| *B60Q 1/52* | (2006.01) |
| *G01N 33/00* | (2006.01) |
| *G08B 21/14* | (2006.01) |
| *B60Q 5/00* | (2006.01) |
| *B60Q 1/50* | (2006.01) |

(52) U.S. Cl.
CPC ............ *B60Q 1/52* (2013.01); *G01N 33/004* (2013.01); *G08B 21/02* (2013.01); *G08B 21/14* (2013.01); *B60Q 1/50* (2013.01); *B60Q 5/005* (2013.01)

(58) Field of Classification Search
CPC ............... G08B 21/02; G08B 21/0202; G08B 21/0438; G08B 21/0446; G08B 21/0453; G08B 21/12; G08B 21/14; G08B 21/16; G08B 21/18; G08B 21/182
See application file for complete search history.

(56) References Cited

U.S. PATENT DOCUMENTS

| | | | |
|---|---|---|---|
| 4,992,965 A | 2/1991 | Holter |
| 5,132,663 A | 7/1992 | Strobl |
| 5,682,145 A | 10/1997 | Sweetman |
| 6,057,755 A | 5/2000 | Phillips |

(Continued)

OTHER PUBLICATIONS

USPTO; Notice of Allowance (dated Oct. 11, 2018) in parent U.S. Appl. No. 15/634,920, filed Jun. 27, 2018.

(Continued)

*Primary Examiner* — Van T Trieu
(74) *Attorney, Agent, or Firm* — Robert H. Frantz

(57) ABSTRACT

One or more noxious gas detectors disposed within a cabin of a vehicle are used by an analyzer to determine that a rate of increase of measured noxious gas exceeds a first threshold, or that a level of measured noxious exceeds a second threshold, or both; and to generate an alert output responsive to the determination. Optionally, the analyzer may take remediation actions by emitting or transmitting commands to the vehicle's control computer to stop or start the engine, start the air conditioning or heater, roll down windows, unlock doors, activate horns and lights, and even transmit alert messages to one or more recipients. In one embodiment, a window clip-on sign is provided with one or more sensors on an interior portion of the unit, and one or more alert means on an exterior portion to provide a portable and easy-to-use safety device.

16 Claims, 14 Drawing Sheets

(56) References Cited

U.S. PATENT DOCUMENTS

| | | | |
|---|---|---|---|
| 6,104,293 A | 8/2000 | Rossi | |
| 6,208,256 B1 | 3/2001 | Fleming | |
| 6,448,888 B1 | 9/2002 | Horner | |
| 6,768,420 B2 | 7/2004 | McCarthy et al. | |
| 6,812,825 B1* | 11/2004 | Volk | G07C 5/006 340/309.16 |
| 6,902,284 B2 | 6/2005 | Hutzel et al. | |
| 7,109,853 B1 | 9/2006 | Mattson | |
| 8,803,677 B1* | 8/2014 | Miller | G08B 21/14 340/438 |
| 8,803,696 B1 | 8/2014 | Dunyan | |
| 9,311,805 B2 | 4/2016 | Zishaan | |
| 9,403,437 B1 | 8/2016 | McDonald et al. | |
| 9,443,411 B2 | 11/2016 | Schoenberg | |
| 9,738,222 B2 | 8/2017 | Hathaway | |
| 9,752,436 B2 | 9/2017 | Pavetic | |
| 9,758,015 B2 | 9/2017 | Baron | |
| 9,845,050 B1* | 12/2017 | Garza | G08B 21/0205 |
| 2002/0145522 A1 | 10/2002 | Pembroke | |
| 2010/0298683 A1 | 11/2010 | Cabrera | |
| 2015/0279169 A1* | 10/2015 | Pretta | G08B 5/36 340/670 |
| 2016/0272112 A1* | 9/2016 | DeGrazia | B60Q 9/00 |
| 2016/0304028 A1 | 10/2016 | Hathaway | |

OTHER PUBLICATIONS

Valdes-Dapena, P.' GM Unveils new feature to prevent child death in hot cars, retrieved Apr. 23, 2017 from http://money.cnn.com/2016/06/13/autos/gmc-child-back-seat-reminder/.

Sashin, D.; "Walmart announces infant car seat designed to prevent hot car deaths"; retrieved on Apr. 23, 2017 from http://www.cnn.com/2015/07/24/health/walmart-car-seat-hot-car-deaths/1.

Babyalert; ChildMinder SoftClip(R) Single System—White', retrieved on Apr. 23, 2017 from https://www.babyalertinfo/childminder-softclip-single-system-white.html.

Aviso Reminder Systems; "2017 Update", retrieved on Apr. 23, 2017 from http://avisoreminder.com.

CO2Meter; "USB Communication Protocol for CO2mini", retrieved on Jun. 26, 2017 from www.co2meters_com/Documentation/AppNotes/AN135-CO2mini-usb-protocol.pdf.

Drivers Little Helper; "How it works"; retrieved on Apr. 23, 2017 from https://driverslittlehelper.com/pages/how-it-works.

Digikey; "Product Index > Sensors, Transducers > Gas Sensors", retrieved on Jun. 26, 2017 from https://www.digikey.com/.

CO2Meter; "CO2Mini indoor air quality monitor", retrieved on Jun. 26, 2017 from https://www.co2meter.com.

Recharge; "Safety of lithium-ion batteries", retrieved on Jun. 26, 2017 from www.rechargebatteries.org/wp-content/.../ Li-ion-safety-July-9-2013-Recharge-.pdf.

IRemind; "FAQ", retrieved on Apr. 23, 2017 from http://www.sunshinebabyalarm.com/faq/.

CBSNews; "Gov't Study: Devices that alert parents they left a child in car deemed unreliable"; retrieved on Apr. 23, 2017 from http://www.cbsnews.com.

FOX4News; "10-year-old McKinney boy creates fan to help prevent hot car deaths"; rerieved on Jun. 26, 2017 from http://www.fox4news.com.

Lamansky, K.; "Teen develops car seat alarm system to prevent hot car deaths", retrieved on Apr. 23, 2017 from http://wqad.com.

Pawlowski, A.; "Inspired by baby, engineer mom invents gadget to prevent kids dying in hot cars"; retrieved on Apr. 23, 2017 from http://www.today.com.

NHTSA; "Reducing the potential for heat stroke to children in parked motor vehicles: Evaluation of reminder technology", Jul. 2012, DOT HS 811 632.

CO2Meter; "CO2Mini CO2 Monitor User Manual"; retrieved on Jun. 26, 2017 from co2meters.com/Documentation/Manuals/Manual-RAD-0301.pdf.

USPTO; first office action (dated Apr. 20, 2018) mailed in parent U.S. Appl. No. 15/634,920, filed Jun. 27, 2018.

Gage, Michael T., et al.; response to first office action (dated Jul. 20, 2018) submitted in parent U.S. Appl. No. 15/634,920, filed Jun. 27, 2018.

* cited by examiner

US 10,457,200 B2

ABANDONED OCCUPANT DANGER ALERT SYSTEM

FIELD OF THE INVENTION

This patent application is a continuation-in-part of patent application Ser. No. 15/634,920, our docket MGRF2017001, filed on Jun. 27, 2017, now U.S. Pat. No. 10,217,344. The invention generally relates technologies to detect and optionally remediate the presence of and/or the rise in levels of dangerous and hazardous gases in a vehicle which may indicate a child has been abandoned in a vehicle, the driver may be in danger of impaired operator driving, or other undesirable situations may exist or be imminent.

BACKGROUND OF INVENTION

Noxious gasses within a vehicle interior can lead to impaired or drowsy driving, and even death in the short term, and in the longer term, may lead to a variety of illnesses of the occupants such as pulmonary issues, allergies, and the like. Noxious gasses can be produced from within the vehicle by the materials used in the vehicle, such as plastics, flame retardants, by the human or animal occupants, and can be introduced into the cabin from the exterior of the car by the ventilation system.

SUMMARY OF THE INVENTION

One or more noxious gas detectors disposed within a cabin of a vehicle are used by an analyzer to determine that a rate of increase of measured noxious gas exceeds a first threshold, or that a level of measured noxious exceeds a second threshold, or both; and to generate an alert output responsive to the determination. Optionally, the analyzer may take remediation actions by emitting or transmitting commands to the vehicle's control computer to stop or start the engine, start the air conditioning or heater, roll down windows, unlock doors, activate horns and lights, and even transmit alert messages to one or more recipients. In one embodiment, a window clip-on sign is provided with one or more sensors on an interior portion of the unit, and one or more alert means on an exterior portion to provide a portable and easy-to-use safety device.

BRIEF DESCRIPTION OF THE DRAWINGS

The description set forth herein is illustrated by the several drawings.

DETAILED DESCRIPTION OF EMBODIMENT(S) OF THE INVENTION

The inventors of the present invention have recognized a problem in the art not previously recognized or addressed regarding detection of, alerting to and remediation of noxious gasses within a vehicle's passenger compartment, also referred to as "cabin." While the several example embodiments described herein will relate to temperature and carbon dioxide ($CO_2$) within a passenger car, truck or van, those ordinarily skilled in the art will readily recognize that the invention may just as well be adapted to and embodied for other gasses and other vehicle types, such as trains, airplanes, and another other scenarios in which human occupants are contained within limited volumes of atmosphere.

Detection of Abandoned Occupant(s)

"Hot Car" deaths of children and pets refers to scenarios in which adult drivers of a vehicle leave a child or pet in a car for a period of time in which the vehicle is turned off, the windows are essentially closed, and the air conditioner is disengaged. The present inventors have realized that previous attempts at detecting abandoned occupants have failed to meet the need in the art because they are based on detection of weight and/or physical movement in a car seat, baby seat, or booster seat. Further, infrared (heat) detection of occupants can fail because hot car interiors can cause too much background noise (heat) above the heat of the human body, rendering the passive infrared (PIR) detectors inaccurate. So, despite numerous attempts by others in the market, countless children and pets die while abandoned in hot cars.

Figure 2:
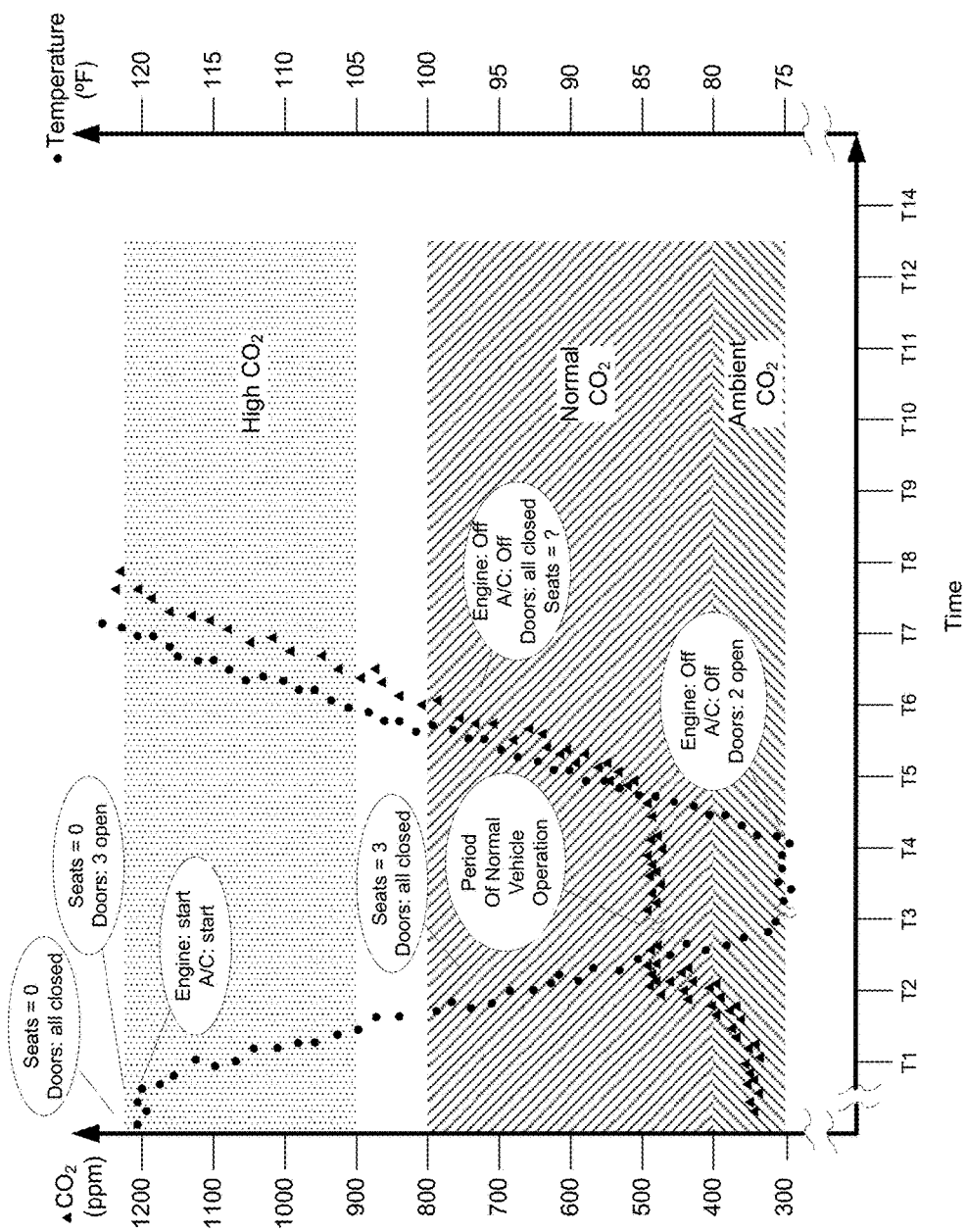
FIG. 2 provides an example profile of discrete (digital) temperature and $CO_2$ measurements during a variety of vehicle state changes.

Turning to FIG. 2, illustrative data shows the urgency of the situation when a car is left parked, with the windows rolled up, engine and air conditioning disengaged, and one or more occupants. For example, according to test results obtained by the present inventor, in a vehicle which is empty for a sufficiently long period of time or which has its windows and/or doors open for a sufficiently long time, the $CO_2$ levels will drift down to ambient levels, such as between 300 and 400 ppm, as shown near the origin ($T_0$) in FIG. 2. Temperature in the interior of the vehicle, however, on a hot day, may exceed the ambient (exterior) temperature because of the thermal gain produced by the greenhouse effect of the windows of the vehicle, so in this illustration, interior temperature begins at 120 degrees Fahrenheit (° F.). At the beginning of this scenario, no seats are occupied, and all doors are closed, followed by two doors being opened, then engine being started, and the air conditioning (A/C) being turned on (engaged). In many vehicles, these vehicle state changes can be collected by an analyzer as they are detected by signals from switches, commands from controls, etc., often carried on a data bus within the vehicle, which will be discussed in more detail later in this disclosure.

Following these vehicle state changes, the interior temperature begins to fall due to the A/C's effect, and the $CO_2$ level begins to rise due to the exhalations of the two occupants. In some embodiments, vehicle state signals may be available to the analyzer to see that weight is present in two seats, which correlates well to the two doors having been opened and then closed. After a period of normal vehicle operation, shown by the S-shaped break marks in the series of discrete data samples, the interior $CO_2$ levels typically will have stabilized around 450 to 600 ppm, depending on how much exterior air is brought in by the A/C, the fan speed of the A/C, the tightness of the vehicle's cabin (e.g., fit of gaskets around doors, windows, etc.), whether or not any windows are partially open, and the physiology of the occupants (e.g., lung capacity, respiration rate, whether or not they are talking, etc.). The present inventors, however, have realized that the relatively stable level of $CO_2$, rather than the absolute level, can be used to determine a "normal" level of $CO_2$ with the necessity of knowing more about the occupants, shape of the volume of the vehicle interior, A/C configuration, etc. Instead, an innovative way of detecting a potentially dangerous noxious gas situation is to start by determining a normally safe situation by detecting relative shifts between ambient conditions and normal operating-and-occupied conditions.

Continuing in FIG. 2, when the engine is shut off and the A/C is disengaged, and perhaps after one door is reported as opening and then closing, the inventors' tests indicated that a five-person mid-size sedan would see a rapid rise of temperature to dangerous conditions within 6 to 12 minutes. The inventors also discovered that the $CO_2$ levels also rapidly rise during this time, the rate of increase being somewhat dependent of the size and number of occupants still in the car. These occupants would now be considered abandoned, such as a child or pet, and in extreme danger of injury or death.

So, the solution devised by the present inventors performs these digital measurements, adaptively determines the relative levels of ambient and normal operating and occupied conditions, optionally using vehicle signal states to confirm vehicle conditions, and provides an alert to a plurality of outputs to elicit immediate assistance to the abandoned occupants. Optionally, the safety device would perform one or more automatic remediation actions, such as commanding the vehicle to roll down one or more windows partially or fully, to start the engine and engage the air conditioner (or heater in cold environs), to unlock the doors, to sound the horn, to flash interior and/or exterior lights, and to send a variety of messages to notify one or more owners, operators, friends, and/or authorities of the urgent need for rescue. More details of various embodiment options will be provided in the following paragraphs. However, in this manner, through analysis of the levels and rate of change (profiles) of $CO_2$, optionally coupled with analysis of temperature levels and rate of change (profiles), and further optionally with consideration of vehicle state signals to determine changes in the vehicle conditions, are used to detect a potentially abandoned and endangered occupant without the need for movement detection or weight-in-seat detection.

Impaired Driving Warning

Even when the vehicle is in operation and occupied, even with the A/C or heater fully engaged, extrinsic research shows that $CO_2$ levels about 900 ppm can render the driver of the vehicle drowsy, reducing his or her response times, and potentially leading to a vehicle crash. The present inventors' own testing confirmed that $CO_2$ levels can rapidly rise from normal levels, such as 400 ppm to 700 ppm, to way above drowsy levels, such as 1200 ppm, within just a few minutes after engaging the "recirculation" option of a typical vehicle air conditioner (or heater) system. Recirculation is often used to boost the temperature effect of the system, whereas previously heated or cooled air is again heated or cooled by the system instead of heating or cooling exterior air being brought into the cabin by the system. It is often engaged, also, when exterior conditions are such that the driver wishes to keep the interior from being contaminated, such as during traffic congestion when exterior vehicle fumes are high, or when driving through particularly dusty or smelly conditions. Elevated levels of other noxious gasses can also lead to impaired cognitive and reflexive skills of the driver.

So, the profiles of FIG. 2 would be essentially unchanged in an example scenario of engaging the recirculation option, except that the temperature would remain within the normal range while the engine remains running, yet the $CO_2$ level would increase at a rapid rate of change.

In one available embodiment of the present invention, the analyzer can use similar adaptive level and rate of change detection, optionally with vehicle state signals, especially the state signal regarding engagement of a recirculation function, to detect the possible impending or actually existing drowsy levels of $CO_2$. The driver can then be alerted accordingly, such as by a bell, chime, indicator light, or audible message, and optionally, automatic remediation actions can be taken by the embodiment of the invention, such as commanding disengagement of the recirculation function, commanding windows to be partially or fully opened, or even commanding the shutdown of the engine or vehicle in an orderly and safe manner.

Analyzer Functions

The analyzer can be a specially-adapted computer, an electronic circuit, or some combination thereof. In one embodiment, part of all of its analysis, detection, alert generation, and optional remediation actions can be implemented, for example, within one of the several computers already on-board a vehicle, such as a car's On-Board Diagnostic (OBD) system. In other embodiments, it may be provided as separate system, such an after-market accessory, which can be fitted or retrofitted into an existing vehicle.

Figure 3:
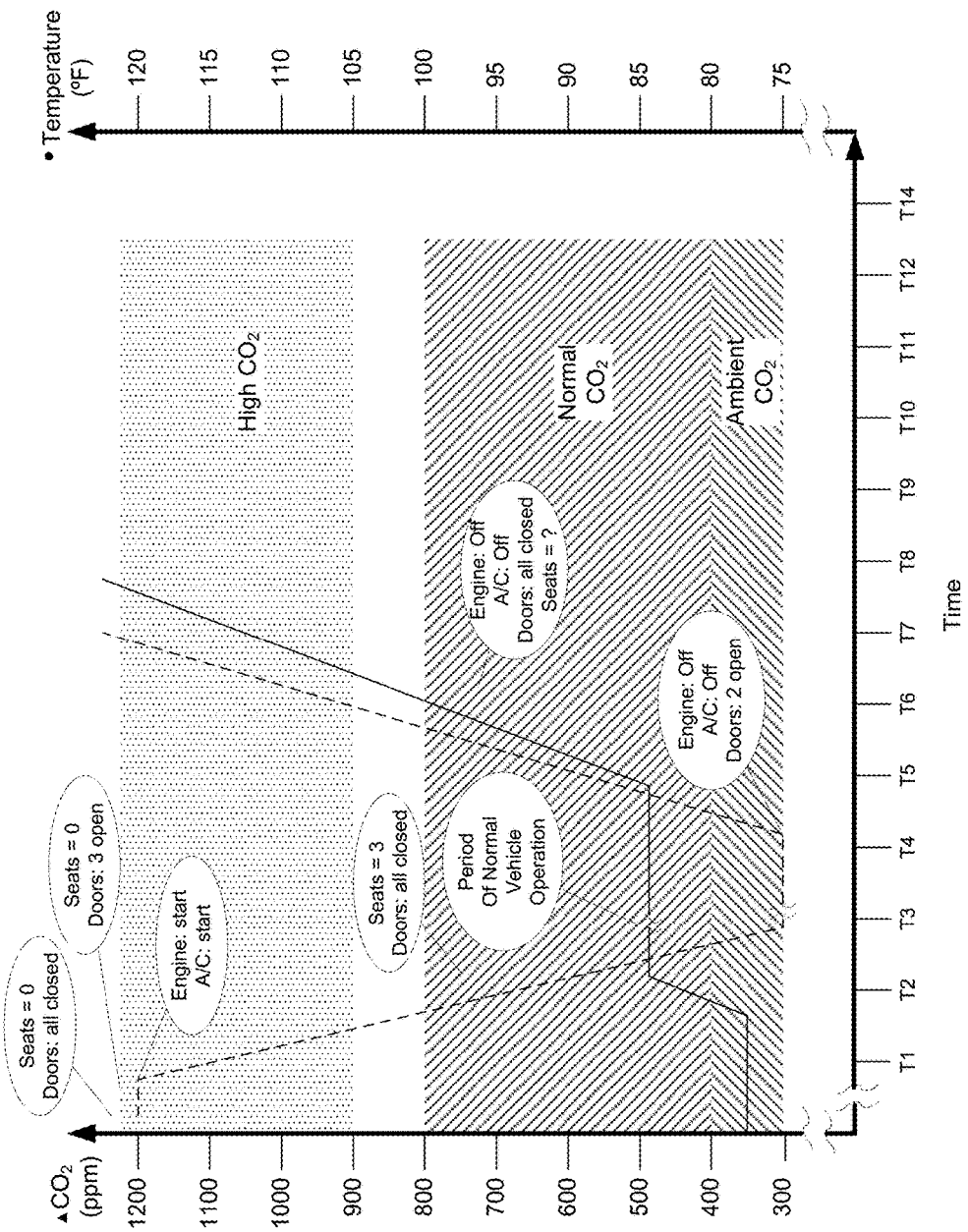
FIG. 3 depicts the example profile of FIG. 2 in which the sets of data samples have been linearized through a numerical method performed by an analyzer computer, electronic circuit, or both.
Figure 4:
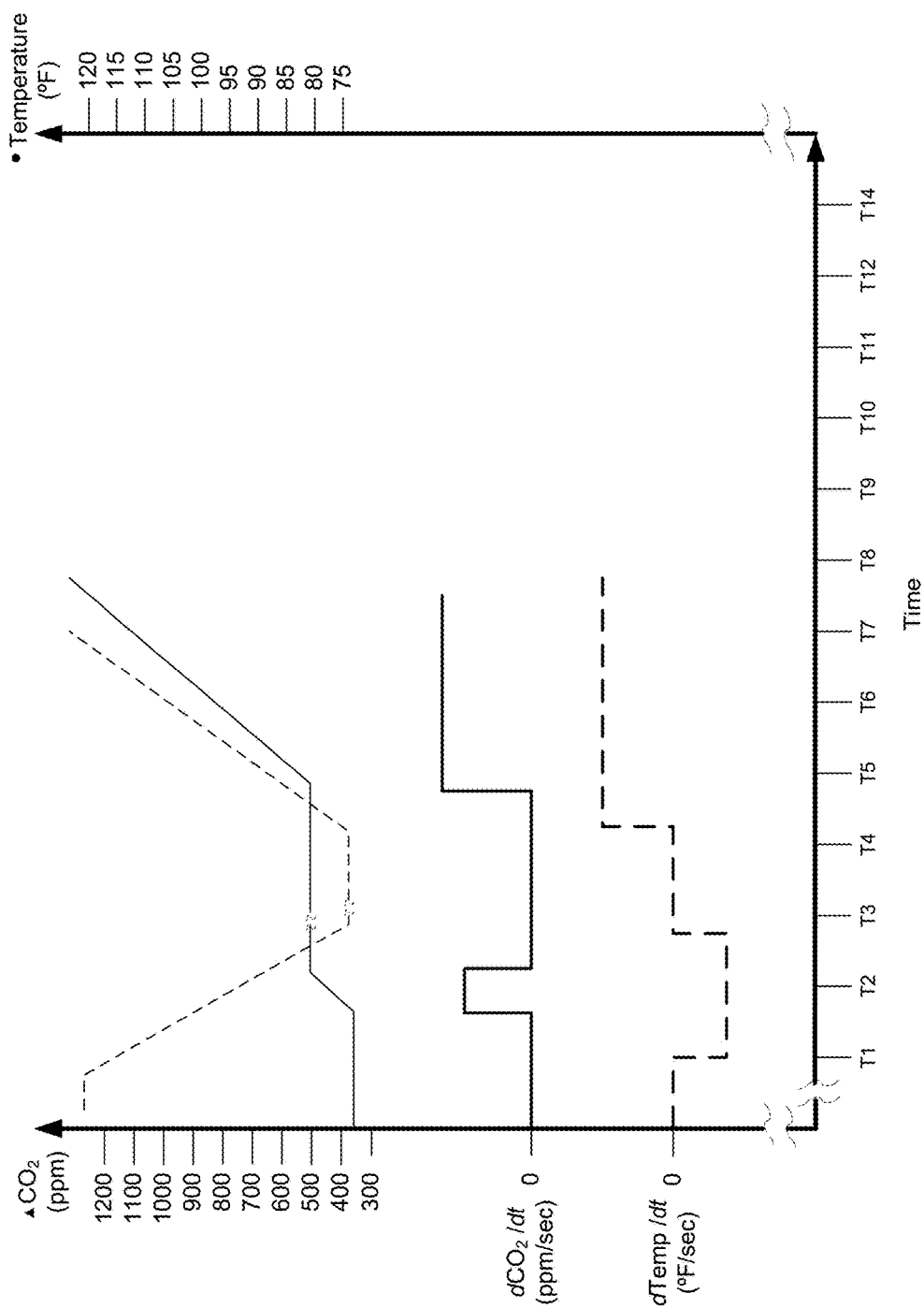
FIG. 4 illustrates the determination of a rate of change of each linearized measurement of FIG. 3 as just one example embodiment available within the scope of the invention.

Linearization Analysis. One embodiment of the present invention linearizes the sample data collected from the $CO_2$ detector, and optionally also from the temperature sensors, as shown in FIG. 3 (a simplified view) relative to the discrete sample plots of FIG. 2. Linearization can be performed by a specialized analysis computer, electronic circuit, or both, using a variety of using a variety of available numerical methods. Piece-meal or step-wise linearization is one available embodiment, in which slopes of the lines represent the rate of change to be monitored for setting off an alert. Such slopes of linear segments can be determined by a specialized computer, electronic circuit, or both, using rate-of-change numerical methods, such as calculating first differential of the measured $CO_2$ levels over time, $dCO_2/dt$, and optionally the rate of change of measured temperature, $dTemp/dt$.

Figure 5:
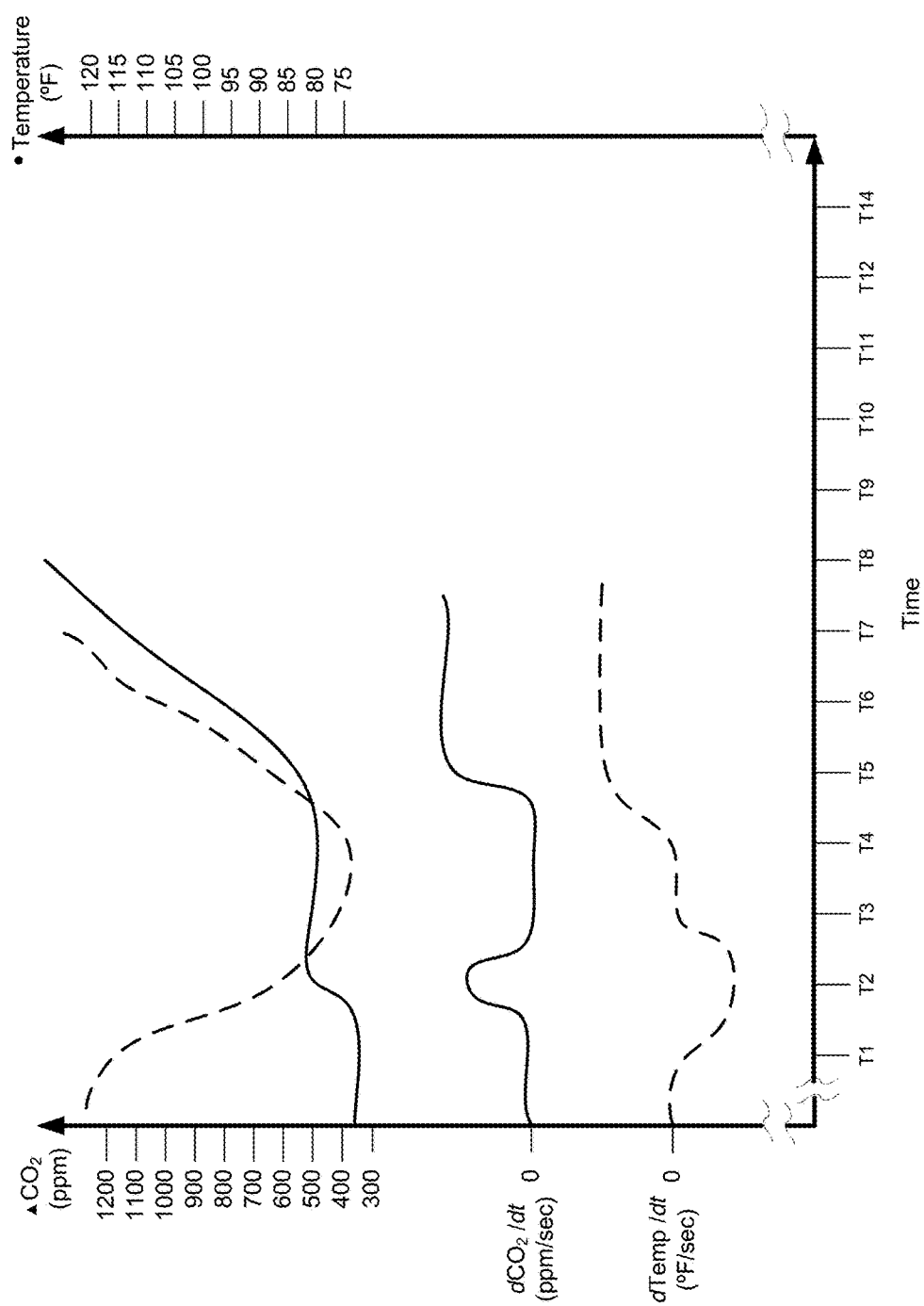
FIG. 5 illustrates another embodiment, within the scope of the invention, in which the sets of data samples of FIG. 2 have been fitted with a curve and the rate of change for each curve has also been determined using a numerical method performed by an analyzer computer, electronic circuit, or both.

Continuous Analysis. While linearization is one option for the analyzer to perform, another embodiment option is to apply curve fitting numerical methods to the data samples to yield smooth, generally continuous digital curves as shown in FIG. 5. There are many known curve fitting numerical methods, each having its own benefits and draw backs, and many of which are superior at reducing noise such as rejecting of spurious data points. With such an embodiment, the rate-of-change calculations would also be smooth, generally continuous digital curves. When certain thresholds, based on the particular noxious gas being measured, are applied to the measured levels (top set of curves) and the rates-of-change (bottom set of curves), this type of analysis may provide earlier and more reliable detection of actual or impending dangerous conditions (e.g., abandoned occupant, drowsy-driving, etc.).

Interfaces

Data Collection. Reception of data samples from various noxious gas sensors, and optionally from temperature sensor(s), can be performed by a variety of digital interfaces, such as a wireless (wi-fi, Bluetooth, infrared data arrangement (IrDA), Zigby, etc.) and wired (Ethernet, USB, CAN, etc.) connections.

Emulation of Wireless Entry Remote Key Fob Functions. One interface to emit the generated alert, and optionally to command the various optional remediation actions, is for the analyzer to emulate the keyless entry functions of a typical vehicle key fob. Via these wireless commands, the analyzer, acting as if it were a remote key fob, can command setting off the horn/alarm and unlocking the doors. In many modern vehicles, the key fob functions also include starting the engine and A/C or heater, rolling down or up windows. And, some vehicles automatically transmit emergency messages, some including global positioning system (GPS) coordinates, when the alarm is activated. As such, one embodiment of the invention which is particularly well suited for aftermarket models is for the analyzer to emulate one or more keyless entry fob commands.

Figure 7:
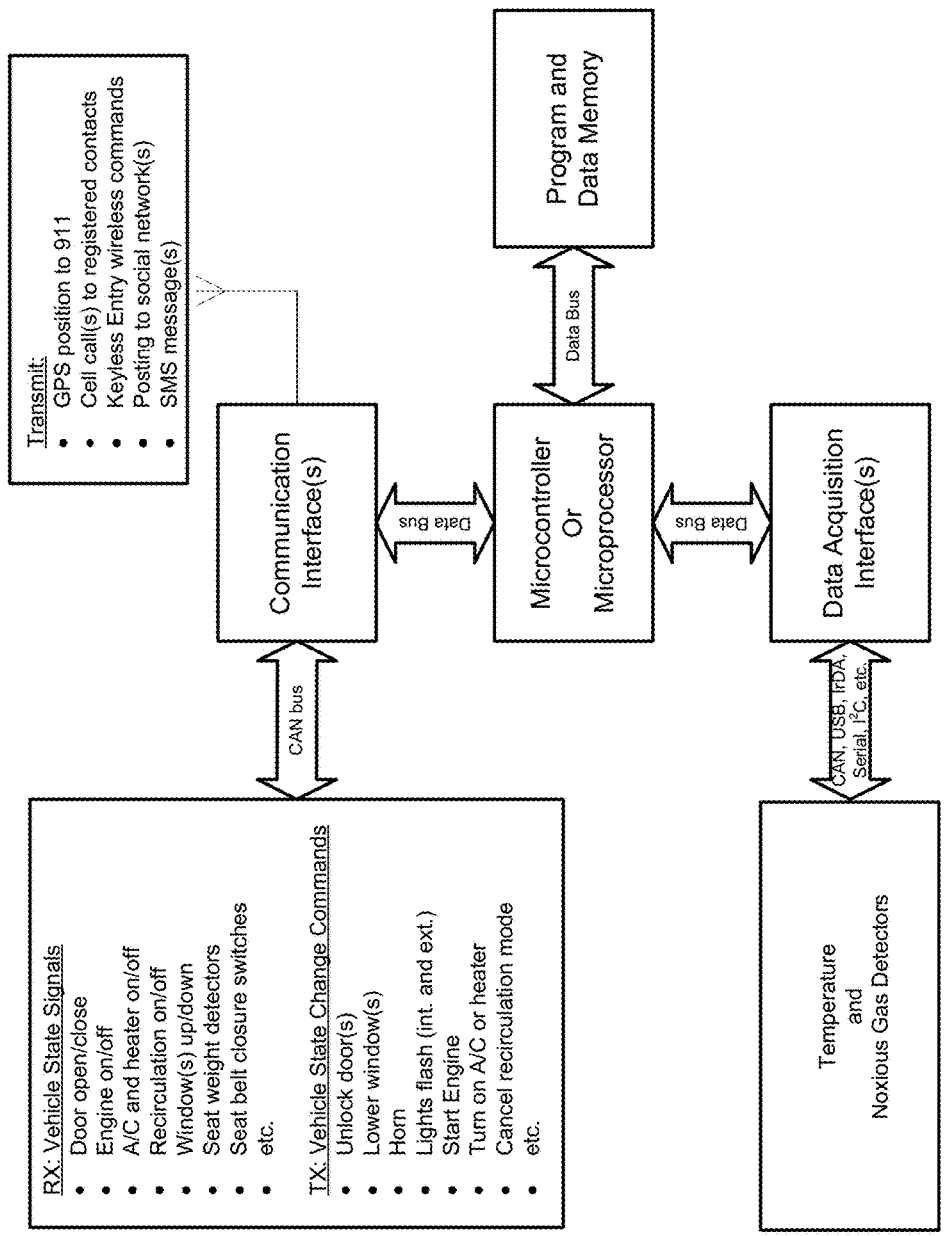
FIG. 7 shows a block diagram of an example embodiment of the invention which interfaces to a vehicle's CAN bus.

Integration to Vehicle Data Bus. Another interface available to some embodiments of the present invention is for the analyzer to connect directly to a digital control bus, such as a Control Area Network (CAN) bus or other digital bus, within a vehicle. In many vehicles, such a digital bus not only allows for commanding of the remediation and alerting functions from the analyzer, but may also allow for collections of the vehicle state signals such as door and window status, engine status, recirculation mode status, seat occupancy relay status, seat belt connected status, etc. An embodiment such as this is illustrated in FIG. 7, which includes a microprocessor and memory, one or more data acquisition interfaces, one or more communications interfaces, and one or more temperature and noxious gas detectors or sensors.

It is possible to combine keyless entry wireless commands and vehicle digital bus interface functions to achieve even greater levels of operability and utility.

Correlation of Multiple Sensors

Figure 6:
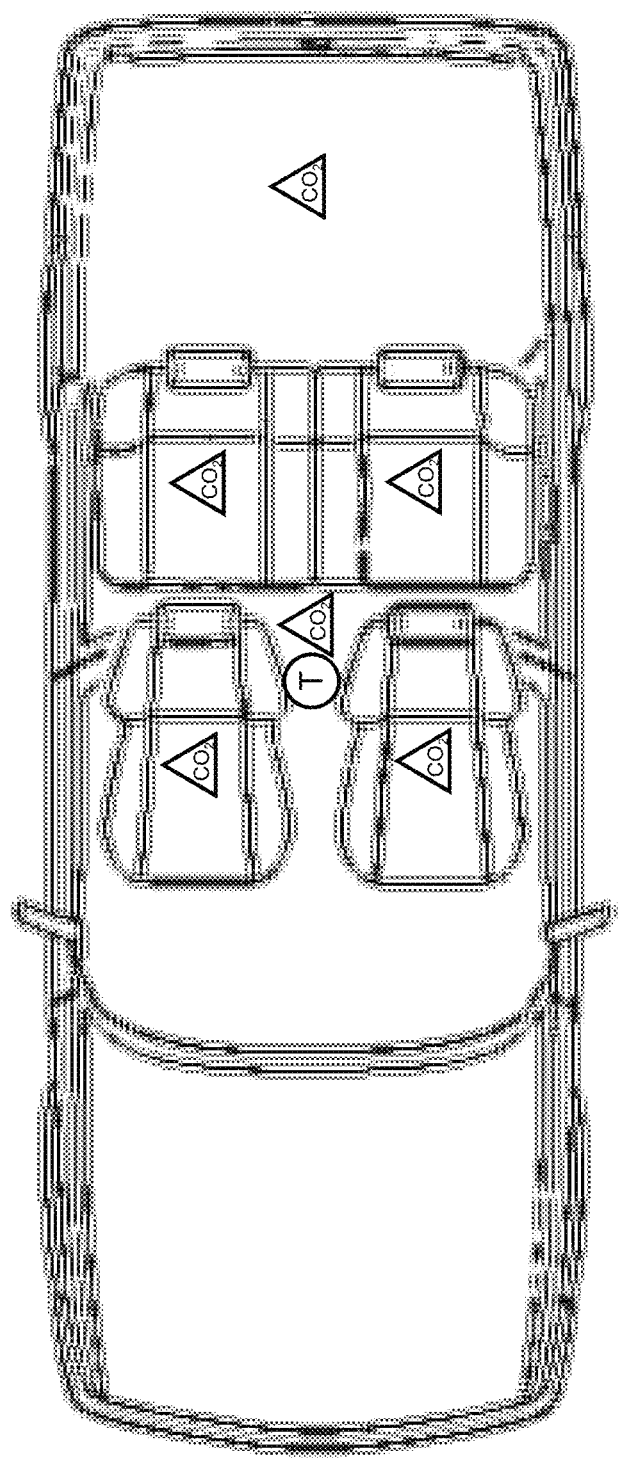
FIG. 6 provides an example topology of the placement of various CO2 and temperature sensors within a five-passenger vehicle.

Turning to FIG. 6, a plurality of locations of CO2 (triangles) and temperature sensors (circles) are shown for an exemplary five-person vehicle. At minimum, one noxious gas sensor is recommended for an embodiment. With multiple noxious gas sensors, further correlation between levels and rates of change of the sensors can be performed by the analyzer to confirm alerting conditions or to eliminate spurious readings.

For example, if the rear seat contains two $CO_2$ sensors, one above or near each of the passenger and driver sides, then a rapid rise in $CO_2$ at one seat may be correlated to a slower but measurable rise in the adjacent seat. And, if a sensor is placed at or near the driver's seat, then a lack of normal level $CO_2$ at the driver's seat may further be used to confirm an abandoned occupant situation. Additionally, since in many scenarios the driver will open and close the driver's door upon existing the vehicle which will lower the $CO_2$ level near the driver's seat, if the driver's $CO_2$ level is near or falling towards ambient but a rear seat $CO_2$ level is rising towards an upper threshold, the analyzer's logical process can consider this and use it as confirmation that an occupant in the rear seat has been left in a non-running car.

Variations and Enhancements in the Exemplary Embodiments

The foregoing exemplary embodiments are provided to illustrate how the invention solves the problem in at least a few scenarios, but they do not define the boundaries of the present invention. Many embodiment variations are foreseeable, some of which are now discussed.

Noxious Gas Detectors. At minimum, a single noxious gas detector may be used to provide a useful alerting and optional remediation system. The analyzer can provide an alert simply by the level of the gas detected, or by the rate of change of the measured gas, or a combination of both level and rate of change. The noxious gas sensors may include one or more, and in some embodiments a combination of several different gas detectors. Besides $CO_2$ which is exhaled from occupants, $CO_2$ may also be emitted by components of the vehicle, such as plastics and hybrid vehicle lithium-ion batteries. As such, various embodiments of the present invention contemplate incorporation of gas detectors and appropriate thresholds for each, including but not limited to detectors for carbon dioxide, a carbon monoxide, benzene, methane, ethylene, ethane, propylene, hydrogen flouride, and nitrogen.

Detector Locations. When a plurality of detectors are used in an embodiment of the invention, they may be advantageous dispersed and located throughout the passenger cabin of a vehicle, as well as optionally within various other compartments, such as a trunk, luggage compartment, or toilet area, which which noxious gasses may emit or be detected. When multiple detectors are employed, their relative locations can be used by the analyzer to correlate emptiness of some passenger seats and occupied status of other passenger seats through the detection of or lack of cross-gas measurements.

Vehicle State Signals. In the foregoing examples, certain vehicle state signals were described as being optionally utilized by the analyzer to confirm alert conditions, or to reduce false alarms. Other embodiments may advantageously receive vehicle state signals including some or all of a door open signal, a door closed signal, a heater on signal, a heater off signal, an air conditioning system on signal, an air conditioning off signal, a cabin fan on signal, a cabin fan off signal, a recirculation mode engaged signal, a recirculation mode off signal, an cabin temperature signal, an engine running signal, an engine off signal, a window up open, a window closed signal, a seat occupied signal, and a safety belt status signal.

Vehicle State Change Commands. In the foregoing examples, certain vehicle state change commands to generate the alert and optionally to produce a remediation action were described as being optionally generated and transmitted by the analyzer. Other embodiments may advantageously generate and transmit vehicle state change commands including some or all of an audible alert, a horn, a buzzer, a chime, a visual alert on a display, an interior light-flashing control, and exterior light-flashing control, an unlock door control, an open window control, an engine start control, an engine stop control, an environmental systems engage control, a recirculation disengage control, a short message service (SMS) message transmission, a global position system location indication transmission, a social media post transmission, and a cellular telephone call.

Noxious Gas and Temperature Thresholds. In the foregoing examples, certain thresholds were disclosed to generate the alert and optionally to produce a remediation action. These thresholds were related to $CO_2$ and temperature embodiments which detect abandoned occupants and/or drowsy driving conditions. However, other gasses may also be detected in other embodiments so as to prevent accidental or intentional death by asphyxiation, such as carbon monoxide detector.

So, where the example threshold in one embodiment of the rate of change of $CO_2$ was calculated and used as 900 ppm (more recent rate of change) minus 600 ppm (less recent rate of change) over ten minutes for a threshold rate of change of 30 ppm per minute, other thresholds for levels and rates of changes can be implemented by the analyzer as appropriate for the other noxious gasses being detected. These thresholds are known in the art, such as the June 2013 "Safety of Lithium-Ion Batteries" report from the European Association for Advanced Rechargeable Batteries, which would be useful for implementing appropriate embodiments of the present invention with respect to a hybrid vehicle where the lithium-ion batteries compartment communicates with the passenger cabin.

Logical Processes. Many various logical processes may be implemented within the scope of the present invention to adaptively determine ambient, normal-operation, and dangerous levels of various noxious gasses, and optionally, rates-of-changes for those gasses which should contribute to the alerting and optional remediation actions. These logical processes may be performed by one or more microprocessors running firmware or software, by custom-designed electronic circuits, by programmable logic devices (PLDs), or a combination thereof.

Figure 1:
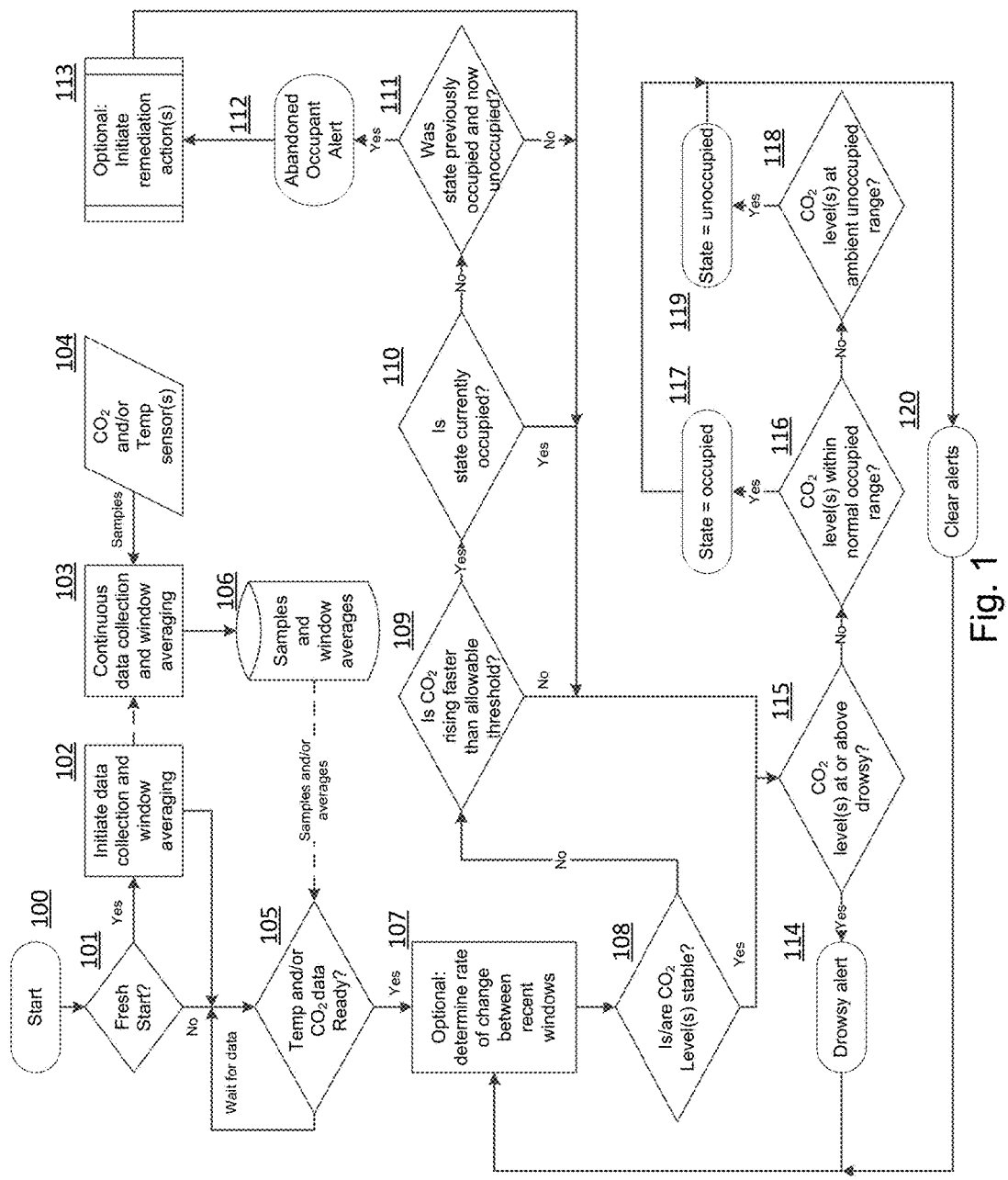
FIG. 1 illustrates an example embodiment of a logical process for execution by an analyzer computer, by a custom electronic circuit, or a combination of analyzer computer and electronic circuit.

FIG. 1 provides an example of one such logical process for a combined system to alert for an abandoned occupant and/or possible drowsy-driving conditions using only $CO_2$ measurements. Other embodiments may use temperature, additional vehicle state conditions, and potentially other gas detectors. This example process starts (100) by determining if the system is initiating for the first time (101) or if it has already been running. If it is initiating for the first time, sensor data collection is started (102) so that it continuously (103) adds new samples (104) and, optionally, averages over a window of time such as 15 seconds to a samples data store (106). Preferably, this collection and averaging process runs independently of the alerting and remediation logic, such as in separate threads or even on separate processors of the analyzer computer.

After the analyzer has waited (105) for the data queue and window averages to be initialized, the analyzer can begin to determine rates of change (107) of each sample set, such as the rate of change of $CO_2$ and rate of change of temperature. If the magnitude of rate of change falls below a certain threshold, then that particular measurement may be deemed as "stable" (108) and thus it is in a "state". If the magnitude of the rate of change exceeds a threshold for a particular data set, then it may be considered to be changing from one state to another, such as changing from ambient to operational-occupied, or from operational-occupied to non-operational-with-abandoned-occupant, etc.

So, if a measurement stable, such as $CO_2$, then the analyzer checks to see if the stable state is above the drowsy threshold (115), such as 900 ppm $CO_2$, within a normal-operational-occupied range (116), such as 400-900 ppm $CO_2$, or within range of an ambient-unoccupied state (118), such as 0 ppm to 400 ppm $CO_2$. If the stable state is within the drowsy range, then a drowsy alert (114) and optionally remediation actions are commanded, and the system returns to consideration of level and rate-of-change analysis results (107). If the state is within ambient-unoccupied or normal-occupied ranges, the appropriate state is recorded (117, 119) for subsequent consideration in the rate-of-change determinations.

If the measured levels are not stable (108), e.g., the window averages show differences exceeding a rate-of-change threshold for that particular measurement, then the analyzer considers (109-111) what state the cabin is transitioning from and transitioning to, and the rate of change it is transitioning states. For example, if a measure level is changing faster than an allowed threshold, such as 30 ppm per minute for $CO_2$, and the state of the vehicle was previously occupied but is now unoccupied (e.g., engine off, one or more doors opened, then doors closed and locked), then an abandoned occupant alert is issued, and optionally remediation actions are commanded by the analyzer because $CO_2$ should not be rising if the vehicle is truly empty of occupants.

As can be seen from this example logical process, certain combinations of conditions can result in both a drowsy alert and an abandoned occupant alert can be achieved, which is a very likely scenario.

Other logical processes, which are inclusive or exclusive of other sensor types, other thresholds, and other vehicle state conditions signals are possible within the range of embodiments of the present invention.

Analyzer Computing Platform

Regarding computers for realization of the specialized analyzer computer, some embodiments may incorporate a computer or embedded microprocessor with requisite memory, processing, and communications capacities. Some embodiments may utilize an operating system, and it may allow for installing of other logical processes to extend, modify or revise the logical processes already on board the analyzer. Specialized co-processors or accelerators, such as graphics accelerators, and suitable computer readable memory devices (RAM, ROM, disk drives, removable memory cards, etc.), may also be incorporated into the specialized analyzer computer. One or more communications and/or network interfaces may be provided, such as Wi-Fi, Ethernet, USB, cellular data, IrDA, etc., as well as specialty interfaces, such as CAN bus, may also be provided in some implementations of the specialized analyzer computer. If the analyzer is intended to interact directly with human users, it may be provided with one or more user interface devices, such as display(s), keyboards, pointing devices, speakers, etc. Each analyzer computing platform may also be equipped with one or more power supplies (battery, AC mains, solar, etc.).

Portable Embodiment

As previously mentioned, the system according to the present invention may be integrated into a vehicle by a vehicle manufacturer, or it may be installed by a qualified technician into an existing vehicle. However, neither of these embodiments may adequately address the portion of the at-risk population which travel in older vehicles, and/or who are transported by different people on different days (e.g., child is dropped off at school or day by mother on Monday through Thursday, but is dropped off by grandmother on Friday's). The present inventors have defined the following exemplary embodiment which is easy to use and portable for just this portion of the at-risk population.

Figure 8:
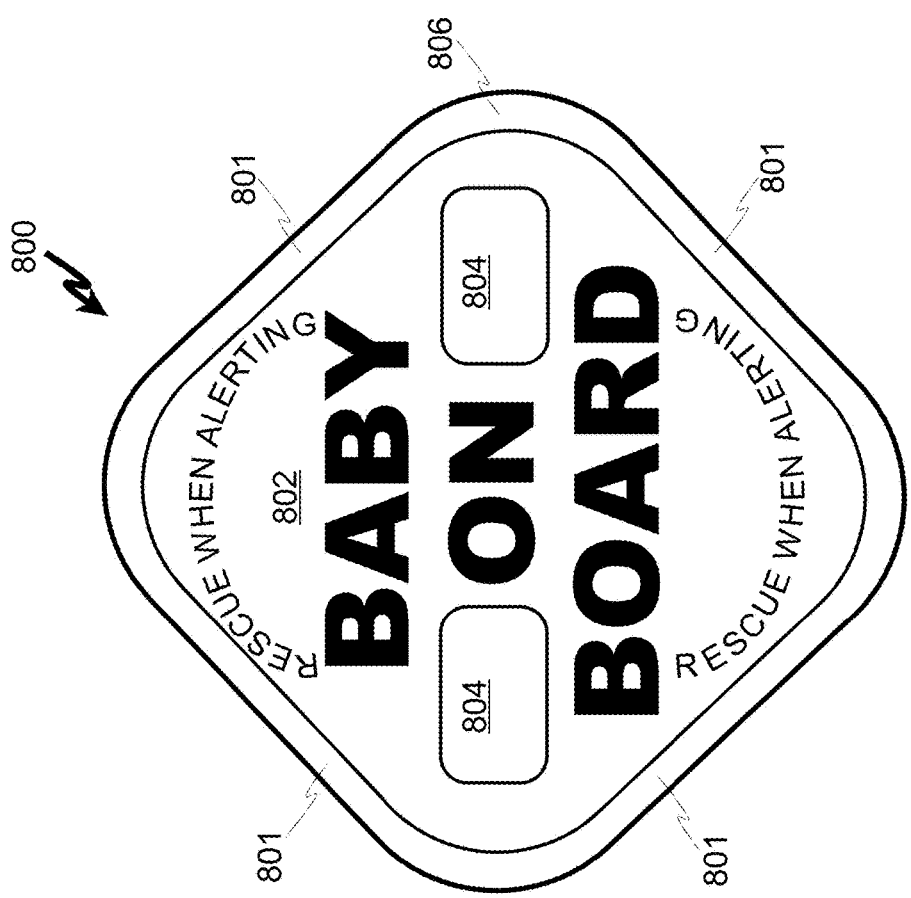
FIG. 8 illustrates the exterior view of a portable embodiment according to the invention.

Referring now to FIG. 8, an exterior view of an embodiment resembling the familiar "Baby on Board" sign as shown. This unit (800) has an exterior face on a front shell (802) on which indicia may be provided, such as "Baby on Board", "Child on Board", "Pet on Board", etc., such as with a yellow background and black lettering. The unit (800) is also provided with a plurality of external alerting means, such as, but not limited to, a translucent ring (801) around the periphery equipped with super bright light emitting diodes (LEDs), strobes, etc. Additionally, the unit (800) may be provided with one or more displays (804), such as a Liquid Chrystal Display (LCD) or digital ink display, and even, in some embodiments, a display for a camera provided with a view inside of the vehicle. Additionally, audible alerting means may also be provided, including some or all of a buzzer, a tweeter, an annunciator, and a voice message speaker. Please note the rightmost corner (106) is marked for orientation to the rest of the diagrams.

Figure 9:
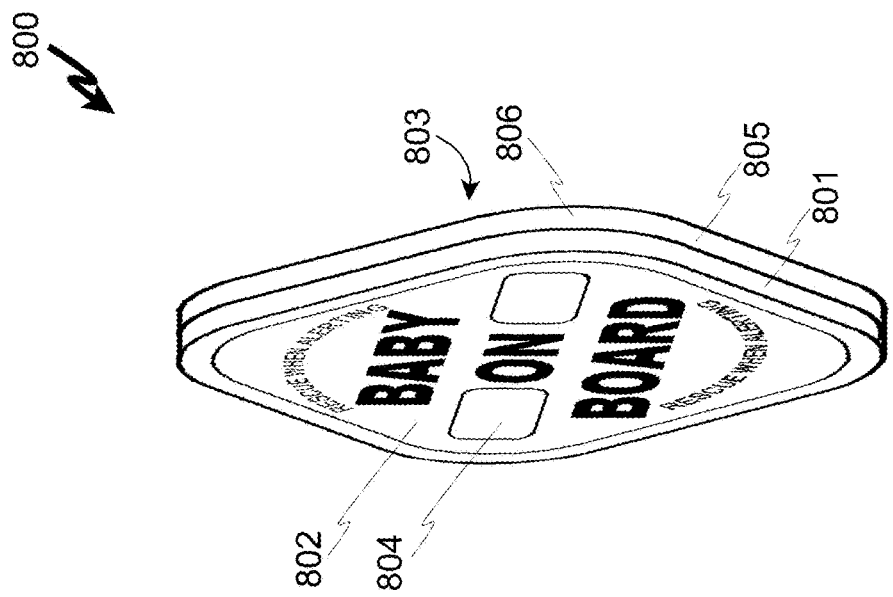
FIG. 9 shows an isometric view of the exterior portion of the exemplary embodiment as shown in FIG. 8 taken from the right-hand side of the exterior portion.

FIG. 9 shows an isometric view of the exterior portion of the unit (800) taken from the right-hand side of the exterior portion. This perspective illustrates one available embodiment having a front shell (802) and a back shell (805) having a back face (803). The shells (802, 805) may snap, glue, or otherwise attach to each other to form the exterior portion of the unit (800), preferably providing a weather-tight seal so as to protect batteries and electronics contained in the space between the shells. From this perspective, one can see that this exterior unit is likely somewhat thicker than the traditional "Baby on Board" sign. Also, one can see that the translucent ring (801) is visible from the side angles as well as from the front view of FIG. 8.

Figure 10:
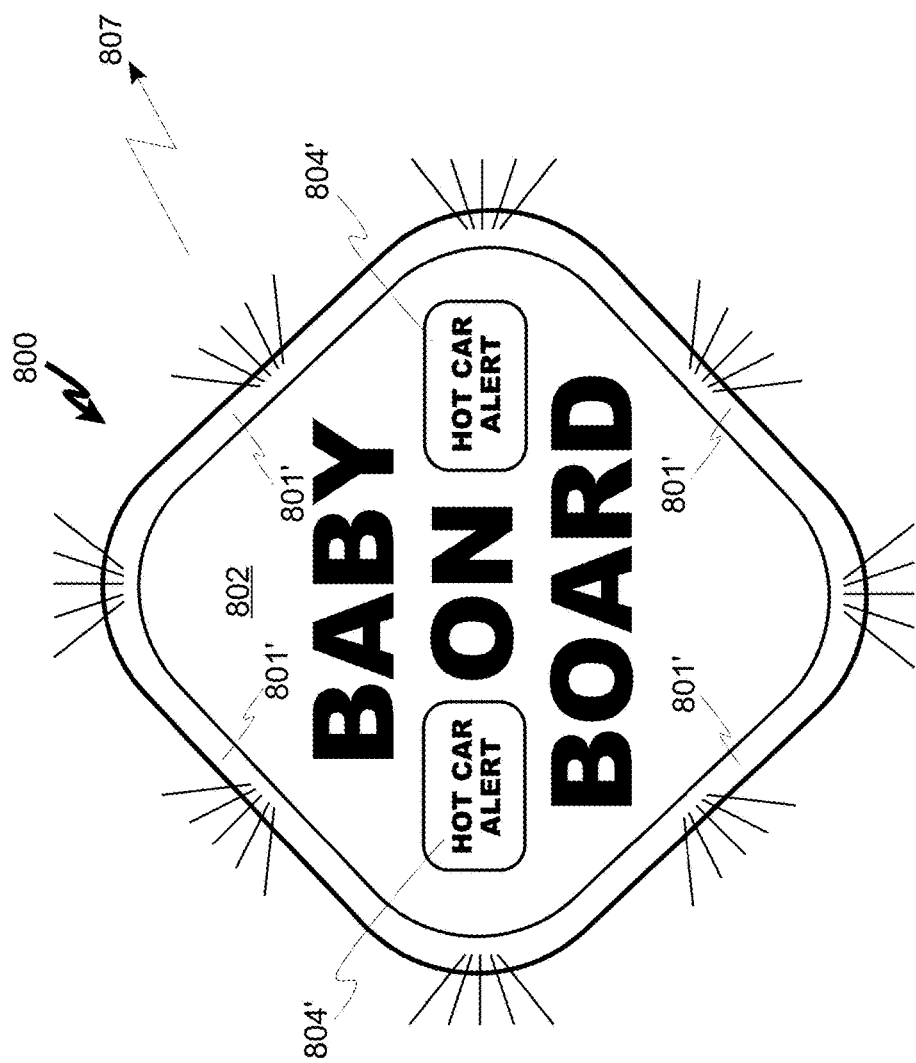
In FIG. 10, a front view of this exemplary embodiment is shown in "alert mode".

In FIG. 10, a front view of this exemplary embodiment is shown in "alert mode", in which the translucent ring is illuminated (801') using super bright LED's or strobes, and the optional digital displays are provided with a preferably sunlight-readable message such as "Hot Car Alert", "Please check for occupants", etc. If this embodiment is provided with an audible alert means, the buzzer, such as a smoke detector buzzer, may be activated, and a voice message may be played through a speaker with audible messages such as those shown on the digital display(s). Still further, in some embodiments, one or more transmissions (807) may be made, such as sending a text message or phone call to an emergency number (e.g., 911 in the USA) or to a registered cell phone number, posting a message on a social media account using a cellular data link, sending a wireless message such as a BlueTooth message to a local telephone, and sending a wireless command emulating a keyless entry fob registered to the car to unlock doors, roll down windows, start engine and climate control, etc. Not all embodiments will be provided with all of these features, in order to allow for cost-reduced versions to reach additional consumers who may not be able to afford the embodiments with the full set of features, of course.

Figure 11:
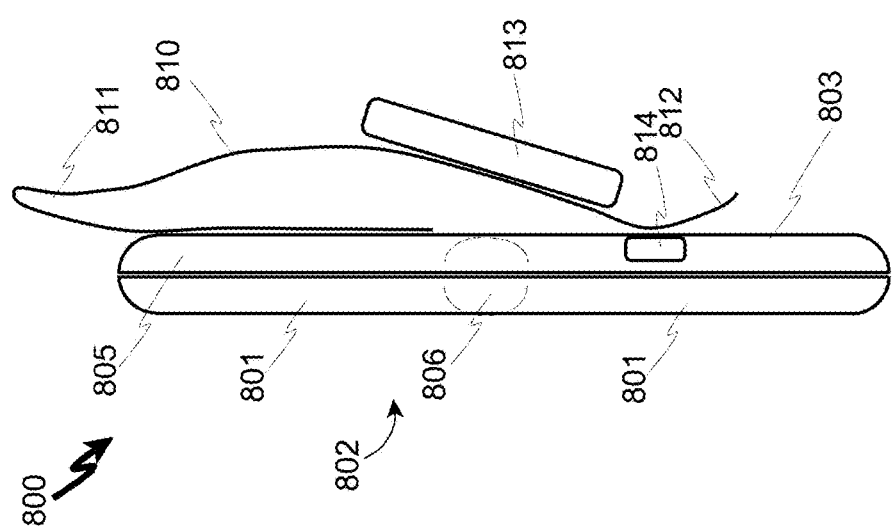
FIG. 11 shows a side view from the right corner to illustrate at least one portable clip-on embodiment according to the present invention.

Referring now to FIG. 11, a side view from the right corner (806) is shown in order to illustrate at least one embodiment of a clip-on mechanism (810) which allows the portable embodiment to be quickly and easily installed on one vehicle and moved to another vehicle. The particular embodiment of the clip, such as a wide flat strip of metal, extends from the back face (803) of the exterior unit extends from the top of the unit into a thin hair-pin curve (811) suitable for being received over the top of a window glass. The clip then descends downward from the curve (811), terminating at a shoe or tongue (812) which is bent at a slight angle from the back face (803) to facilitate slipping the unit (800) over the top of the glass of a car window. A small interior electronics package (813) is attached to the clip (810) to house at least the interior sensor(s) (PIR motion detector, temperature sensor, $CO_2$ sensor, CO sensor, camera, microphone, etc.), and it is preferably wired to the exterior portion where much of the remaining electronics are contained.

Still further, while the unit may have a manual on/off switch, an additional safety measure in some embodiments will be an automatic on/off switch (814) is provided. This switch detects when there is no glass between the back face (803) and the end of the clip (812), and automatically turns off the unit (or puts it into low power mode). The switch (814) automatically engages and arms the detection circuits when it detects glass (or additional space) inserted between the clip (812) and the back face. Many mechanisms are available to achieve this function, not the least of which would be a magnet and a Hall-effect switch, an electrical continuity mechanism, and a recessed switch with a protrusion on the clip which engages the recessed switch. Regardless of the specific means for automatically sensing the clip position, the unit is enabled to automatically engage itself when it is slipped over the top of the glass of a vehicle window.

Figure 12:
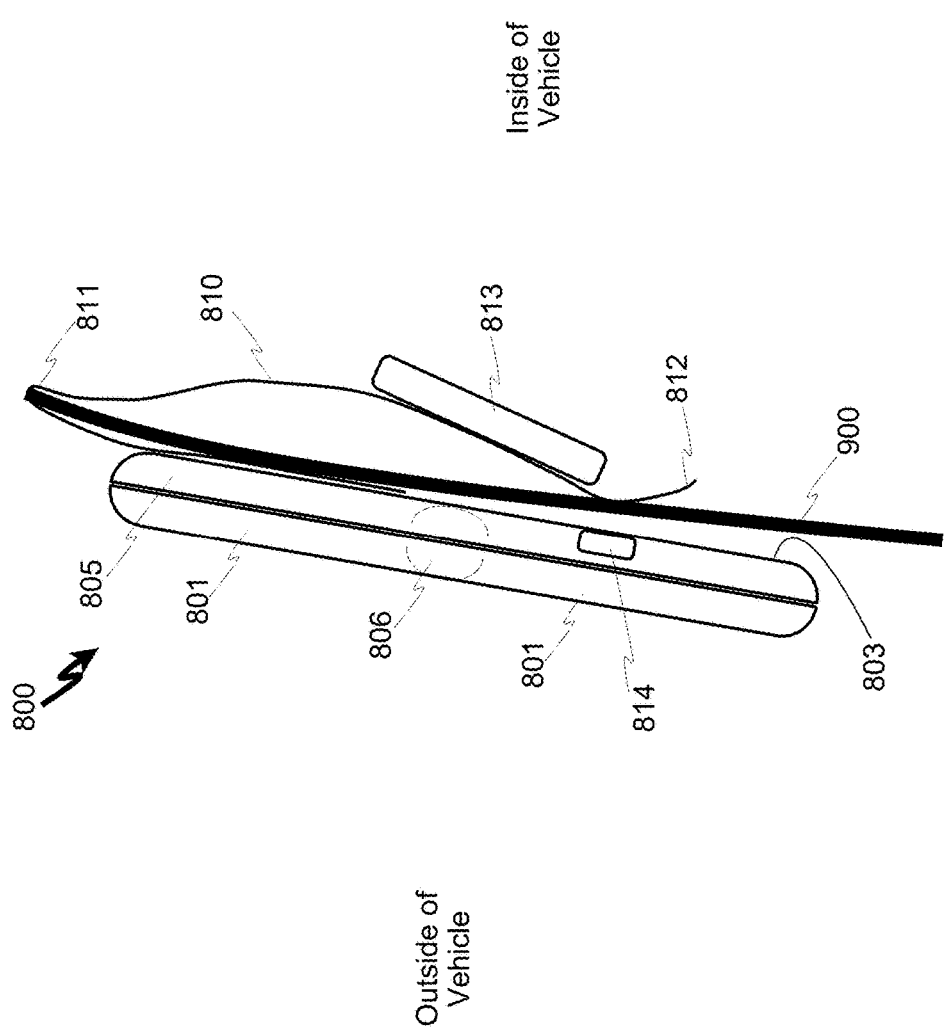
FIG. 12 illustrates an installation onto an upper edge of a vehicle window glass.
Figure 13:
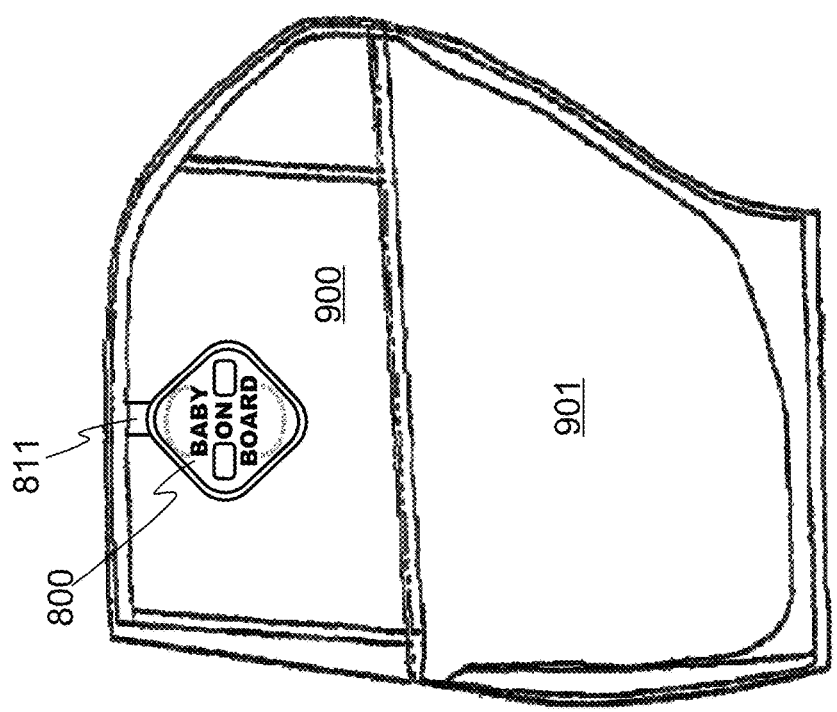
FIG. 13 illustrates how an installation of FIG. 12 might appear on the right rear door of a vehicle.

FIG. 12 illustrates such an installation arrangement, in which the upper edge (900) of a window glass has been received into the clip between the back face (803) and the clip, extending into the curve (811) so that the window can be fully rolled up without interference with the weather stripping around the window. In this installed configuration, one can see the space created between the automatic on/off switch (814) and the end of the clip (812) for an intuitive, safe method of arming the detector and alert. In this arrangement, the exterior face (802) and exterior alerting means (801, etc.) are on the outside of the vehicle where passers-by can be summoned for quick assistance by the alerting means, and the interior sensor package (813) is position within the interior of the vehicle where it can sense gasses, movement, crying, talking, etc., as described elsewhere in this disclosure. FIG. 13 illustrates how such an installation configuration might appear on the right rear door (901) of a vehicle.

Figure 14:
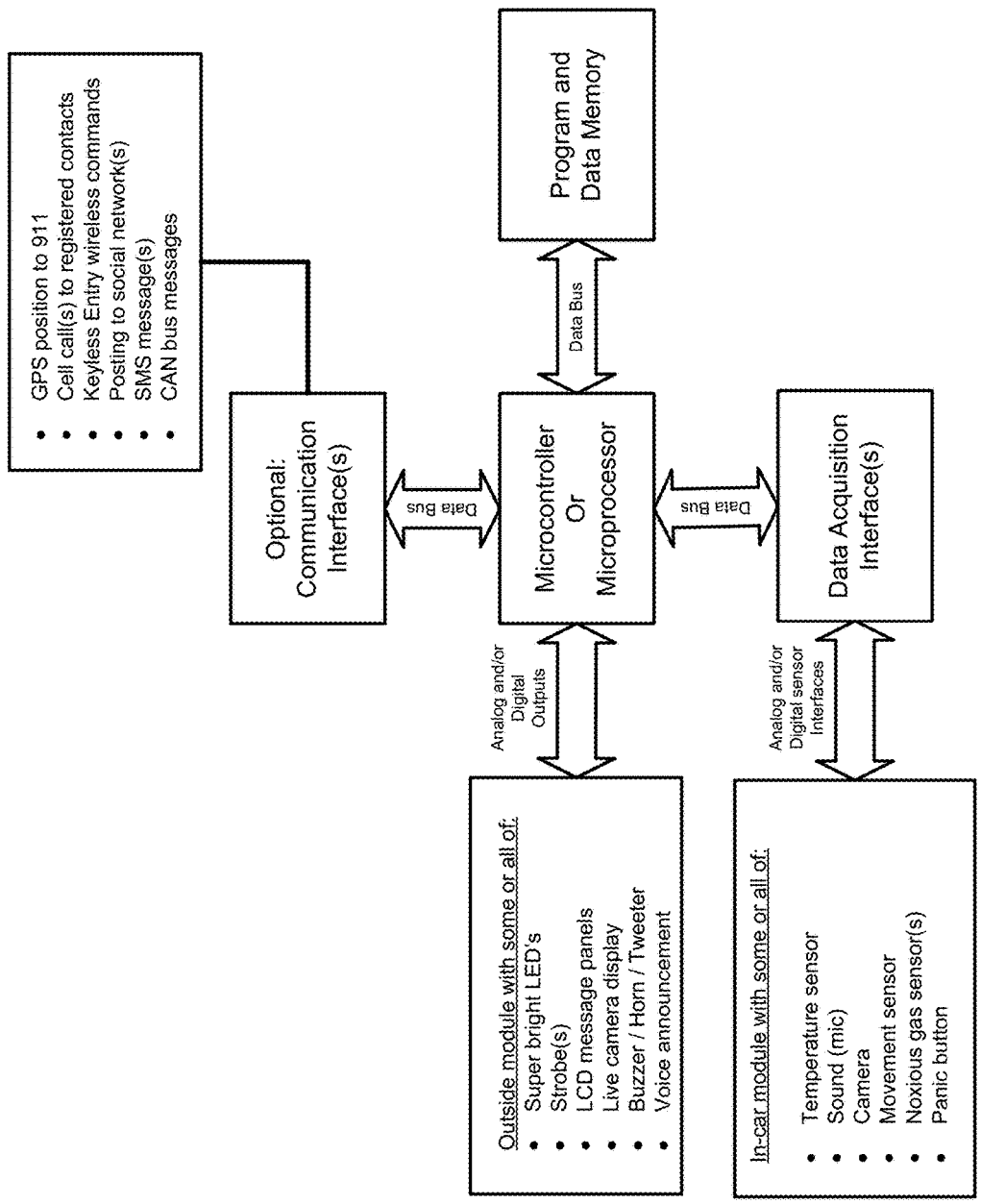
FIG. 14 sets forth a functional block diagram of the portable, clip-on embodiment according to the present invention.

Now referencing FIG. 14, a functional block diagram is shown for this particular exemplary embodiment. It should be noted that this particular embodiment does not require the previously-described $CO_2$ detection and prediction methods, but it preferably does. However, some embodiments may utilize temperature sensors considered with other forms of occupancy detection, such as a passive infrared (PIR) movement detector or other type movement detector (tilt sensor, ultrasonic detector, etc.), a sound or cry detector with a microphone, a panic button, or even a camera with image processing that detects the presence of person or pet or detects a change in scenery.

Also shown in this functional block diagram are optional means of alerting beyond the audible and visible on the exterior of the car, including those previously discussed in conjunction with the $CO_2$ detection process, albeit these may also be engaged in embodiments which omit the $CO_2$ detection means. These may include some or all of calling or message an emergency service via cellular telephone link (e.g., 911 in the USA), making calls or sending messages to telephone number registered to the unit as points of contacts (e.g., owner, relatives, neighbors, co-workers, teachers, etc.), transmitting a keyless entry (key fob) command (e.g., unlock doors, set off car alarm, roll down windows, start engine and climate control, etc.), posting a message to a social media account using a cellular data link (e.g., "tweeting", "instagramming", etc.), and optionally transmitting commands on the car's control bus (e.g., CAN, etc.).

Other Embodiment Variations

The following variations to the external sign embodiment of this invention may be use in place of or in addition to other features as previously described:

(a) other means of attaching the unit components to the exterior of a car include, but are not limited to a magnetic mount, double-sided foam adhesive tape, hook-and-loop fastener, and removable/releasable glue;

(b) other means of communicating between the interior component and the exterior component including iinfrared data arrangement (IrDA), wireless/Radio Frequency, and inductive loop; and (c) other form factor configurations such as a clip-on unit for a car seat, a unit for attaching to posts for a seat head rest, a unit for plugging into a cigarette lighter socket or auxiliary power outlet, and a unit that clips on to a seat belt.

Conclusion

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless specifically stated otherwise.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

It will be readily recognized by those skilled in the art that the foregoing example embodiments do not define the extent or scope of the present invention, but instead are provided as illustrations of how to make and use at least one embodiment of the invention. The following claims define the extent and scope of at least one invention disclosed herein.

We claim:

1. An abandoned occupant alert system comprising:
   an exterior body portion having an exterior face and at least one alerting device;
   at least one noxious gas detector disposed in an interior body portion;
   an analyzer which determines that an alert condition presently exists or will exist within a period of time according to one or more signals received from the at least one noxious gas detector, and which operates the at least one alerting device;
   an attachment device disposed between the exterior body portion and the interior body portion, for receiving the system onto a body component of a vehicle such that the at least one noxious gas detector is in gaseous communication with an interior space of the vehicle, and such that the alerting device is in a position exterior to the vehicle; and
   a switch cooperative with the attachment device for automatically turning on and off at least the alerting device when the system is not attached to a vehicle.

2. The abandoned occupant alert system as set forth in claim 1 wherein the attachment device comprises one or more attachment devices selected from the group consisting of a hook, a clip, hook-and-loop fastener, suction cup, clamp, through-window fastener, and adhesive.

3. The abandoned occupant alert system as set forth in claim 2 wherein the attachment device is configured to attach on, around, or through a window body component of a vehicle.

4. The abandoned occupant alert system as set forth in claim 1 wherein the exterior face has indicia providing instructions for rescue upon operation of the at least one alerting device.

5. The abandoned occupant alert system as set forth in claim 1 wherein the alerting device comprises at least one alert device selected from the group consisting of a light emitting indicator and an audio emitting indicator.

6. The abandoned occupant alert system as set forth in claim 5 wherein the light emitting indicator comprises at least one light emitting indicator selected from the group consisting of a strobe, a ring of light indicators disposed around a periphery of the exterior body portion, a textual display, and a graphical display.

7. The abandoned occupant alert system as set forth in claim 6 further comprising a camera with a range of view into the interior space of the vehicle, and wherein the graphical display communicates an image captured by the camera.

8. The abandoned occupant alert system as set forth in claim 6 wherein the textual display communicates one or more information items selected from the group consisting of primary contact information, instructions for a rescue operation, and secondary contact information.

9. The abandoned occupant alert system as set forth in claim 5 wherein the audio emitting indicator comprises at least one audio emitting indicator selected from the group consisting of a buzzer, a horn, an annunciator, a tweeter, a rumble generator, and a voice-band speaker.

10. The abandoned occupant alert system as set forth in claim 9 wherein the voice-band speaker is modulated to produce a voice announcement.

11. The abandoned occupant alert system as set forth in claim 1 wherein the exterior body portion comprises back face, wherein the switch is further cooperative with the back face.

12. The abandoned occupant alert system as set forth in claim 11 wherein the attachment device comprises a hook, and wherein the switch is configured to turn on at least the alerting device when vehicle window glass is detected between the hook and the back face of the exterior body portion, and to turn off at least the alerting device when no vehicle glass is detected between the hook and the back face.

13. The abandoned occupant alert system as set forth in claim 1 further comprising a transmitter configured to, upon operation of the at least one alert device, transmit at least one signal selected from the group consisting of a short message system (SMS) text message, an emergency cellular phone message, a posting to a social media account, a transmission to a nearby short-range radio receiver, a remote door unlock signal, a remote window lowering signal, a remote vehicle start signal, and a remote vehicle alarm activation signal.

14. The abandoned occupant alert system as set forth in claim 13 wherein the transmission to a short-range radio receiver comprises a transmission to a BlueTooth receiver.

15. The abandoned occupant alert system as set forth in claim 13 wherein the emergency cellular phone message comprises a transmission of a geographical position of the vehicle.

16. The abandoned occupant alert system as set forth in claim 1 wherein the at least one noxious gas sensor comprises a carbon monoxide sensor.

* * * * *